(12) United States Patent
Eeckman et al.

(10) Patent No.: US 8,435,564 B2
(45) Date of Patent: May 7, 2013

(54) PHARMACEUTICAL COMPOSITIONS COMPRISING BRIVARACETAM

(75) Inventors: Frederic Eeckman, Brussels (BE); Monique Berwaer, Brussels (BE); Domenico Fanara, Brussels (BE)

(73) Assignee: UCB Pharma, S.A., Brussels (BE)

( * ) Notice: Subject to any disclaimer, the term of this patent is extended or adjusted under 35 U.S.C. 154(b) by 181 days.

(21) Appl. No.: 12/993,704

(22) PCT Filed: May 28, 2009

(86) PCT No.: PCT/EP2009/056570
§ 371 (c)(1), (2), (4) Date: Dec. 15, 2010

(87) PCT Pub. No.: WO2009/144286
PCT Pub. Date: Dec. 3, 2009

(65) Prior Publication Data
US 2011/0091547 A1   Apr. 21, 2011

(30) Foreign Application Priority Data

May 30, 2008   (EP) ..................................... 08009919

(51) Int. Cl.
*A61K 9/20*   (2006.01)
*A61K 31/40*   (2006.01)
*A61P 25/08*   (2006.01)

(52) U.S. Cl.
USPC .......................................... 424/465; 514/424

(58) Field of Classification Search .................. 424/465; 514/424
See application file for complete search history.

(56) References Cited

U.S. PATENT DOCUMENTS

| 6,106,864 A | 8/2000 | Dolan et al. |
| 2006/0165796 A1 | 7/2006 | Kshirsagar et al. |

FOREIGN PATENT DOCUMENTS

| EP | 1 806 339 A | | 7/2007 |
| WO | 2006/090275 A | | 8/2006 |
| WO | WO 2006/080029 | | 8/2006 |
| WO | WO 2006/090275 | * | 8/2006 |
| WO | 2007/141002 A | | 12/2007 |

OTHER PUBLICATIONS

Von Rosenstiel et al., "Brivaracetam (UCB 34714)", Neurotherapeutics, 4(1), 2007, 84-87.

* cited by examiner

*Primary Examiner* — Blessing Fubara
(74) *Attorney, Agent, or Firm* — McDonnell Boehnen Hulbert & Berghoff LLP

(57) ABSTRACT

The present invention relates to a pharmaceutical composition comprising brivaracetam as active ingredient, the invention relates specifically to a prolonged release formulation.

12 Claims, No Drawings

PHARMACEUTICAL COMPOSITIONS COMPRISING BRIVARACETAM

This application is a US national phase of International Application No. PCT/EP2009/056570 filed on May 28, 2009, which claims the benefit of European patent application 08009919.5, filed May 30, 2008, the disclosures of which are incorporated herein by reference in their entirety.

The present invention relates to a novel pharmaceutical composition comprising Brivaracetam.

International patent application having publication number WO 01/62726 discloses 2-oxo-1-pyrrolidine derivatives and methods for their preparation. It particularly discloses compound (2S)-2-[(4R)-2-oxo-4-propyl-pyrrolidin-1-yl]butanamide known under the international non propriety name of Brivaracetam.

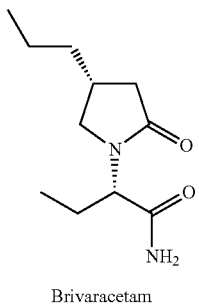

Brivaracetam

Brivaracetam is effective in the treatment of epilepsy. Clinical trials evaluated the efficacy and safety of Brivaracetam (5, 20, 50 and 150 mg per day) in the adjunctive treatment of adult patients (16-65 years) with refractory partial onset seizures, with or without secondary generalization.

One of the objectives currently sought in the development of pharmaceutical compositions which can be administered orally is to control the release of pharmaceutically active substances so that they can be administered in a few daily doses, ideally in a single daily dose.

Brivaracetam is a very water soluble active ingredient (ca. 700 mg/ml), and it is not obvious to slow down the release of the drug.

Moreover another problem consists in the reduction of the release rate, while keeping a reasonable size to the pharmaceutical form given to the patients.

Surprisingly, it was discovered that it was possible to accurately control the release rate of the drug substance so that it can be administered in a few daily doses, and even in a single daily dose and so to provide a therapeutic effect for at least 16 hours when administered to a patient.

Considering Brivaracetam is classified as BCS I, the resulting in vitro dissolution (USP <711> apparatus no 2) in a buffered aqueous media has to show a drug release of no more than 40% after 1 hour of dissolution, of 35%-80% after 4 hours of dissolution and of no less than 80% after 16 hours of dissolution. Preferably, a profile of no more than 35% after 1 hour of dissolution, of 40%-75% after 4 hours of dissolution and of no less than 80% after 16 hours of dissolution. More preferably a profile of no more than 30% after 1 hour of dissolution, of 45%-70% after 4 hours of dissolution and of no less than 80% after 16 hours of dissolution.

The present invention relates to a pharmaceutical composition in the form of a tablet comprising, as active ingredient, Brivaracetam and, as excipient within the core of the tablet, 5% to 80% per weight of at least one hydrophilic matrix agent, with respect to the total weight of the core of the tablet.

The term "active ingredient" as used herein is defined as a substance which has a therapeutic effect.

The amount of the active ingredient present in the pharmaceutical composition of the invention may vary depending on the patient to which the compositions are administered and on the specific disease to be treated.

The term "core of the tablet" as used herein is defined as the pharmaceutical composition without coating. All the percentages are given per weight of the total weight of the core of the tablet, except when it is written otherwise.

The term "hydrophilic matrix agent" as used herein is defined as a pharmaceutical acceptable excipient which generates a gel in contact to water. A "hydrophilic matrix agent" is a material that is a water dispersible rate controlling polymer.

Suitable hydrophilic gel-forming polymers include, but are not necessarily limited to, hydroxypropyl methylcellulose, hydroxypropyl cellulose, methylcellulose, sodium carboxymethylcellulose, hydroxyethylcellulose, and polyethylene oxide. For any given polymer type, use of a material with higher average molecular weight provides higher viscosity in aqueous solution of any given concentration; hence use of a higher molecular weight generally enables use of a lesser quantity of polymer to achieve the required retardation of dissolution. The polymers used are usually those that give a viscosity of more than 100 mPa·s in 2 percent aqueous solution (20° C.), generally more than 250 mPa·s, and preferably more than 500 mPa·s. Preferred hydrophilic gel-forming polymers are selected from hydropropyl methylcellulose, hydroxypropyl cellulose, hydroxyethyl cellulose and polyethylene oxide. Especially preferred is hydroxypropyl methylcellulose having 18-29% methoxyl substitution and 7-10% hydroxypropyl substitution, and having a number average molecular weight of at least 20,000 g/mol. Such polymers include those sold by Colorcon under the tradenames Methocel® K4M, Methocel® K15M, Methocel® K100M and Polyox® WSR.

Other examples of hydrophilic matrix agents which can be used according to the present invention are: noncellulose polysaccharides (galactomannans, guar gum, carob gum, gum arabic, sterculia gum, agar, pregelatinized starch, alginates and the like); polyvinylpyrrolidone; polyvinylacetate; acrylic acid polymers, such as crosslinked acrylic acid-based polymers; and a mixture of two or more of the said agents. The hydrophilic matrix agents may be present in the form of a single compound or in the form of a mixture of compounds.

The hydrophilic matrix agents preferably used according to the present invention are hydroxypropyl methylcelluloses, such as Methocer® K, or polyethylene oxide, such as Polyox® WSR.

Usually, the pharmaceutical composition according to the present invention comprises 5 to 80% per weight of hydrophilic matrix agent with respect to the total weight of the core of the tablet.

Particularly, the pharmaceutical composition according to the present invention comprises 10 to 75% per weight of hydrophilic matrix agent.

Preferably, the pharmaceutical composition according to the present invention comprises 15 to 70% per weight of hydrophilic matrix agent; more preferably 20.0 to 65% per weight of hydrophilic matrix agent; and most preferably 20.0 to 60% per weight of hydrophilic matrix agent with respect to the total weight of the core of the tablet.

Usually the specific surface area of the core tablet is comprised between 2 mm$^{-1}$ and 0.3 mm$^{-1}$. Preferably it is comprised between 1.7 and 0.5 mm$^{-1}$. More preferably, it is comprised between 1.3 and 0.6 mm$^{-1}$. The "Surface Area" is understood to be the ratio between the surface of the core tablet and the volume of the core tablet.

The pharmaceutical composition of the invention may also comprise processing aids such as a gliding agent, lubricant, diluent, and binders, as excipient within the core of the tablets.

The term "gliding agent" as used herein is defined as an agent improving the fluidity of the powder and thus the filling of the granulation machine and the tablet press. The gliding agent may be present in the pharmaceutical composition in the form of a single compound or in the form of a mixture of compounds.

Examples of gliding agents are, but not limited to, talc, starches, stearic acid and anhydrous colloidal silica. Preferred gliding agent according to the present invention is anhydrous colloidal silica, such as Aerosil 200®.

Usually, the pharmaceutical composition according to the present invention comprises 0.0 to 3.0% per weight of gliding agent. Preferably, the pharmaceutical composition according to the present invention comprises 0.0 to 1.5% per weight of gliding agent.

The pharmaceutical composition of the invention may also comprise a lubricant, as excipient within the core of the tablet The term "lubricant" as used herein is defined as an agent able to decrease adhesion of a powder to punches and friction between particles. The lubricant may be present in the pharmaceutical composition in the form of a single compound or in the form of a mixture of compounds.

Examples of lubricants are, but not limited to, talc, magnesium stearate, calcium stearate, poloxamer, sodium lauryl sulfate, stearic acid or macrogol (also referred to as polyethylene glycol or PEG).

Preferred lubricant according to the present invention is magnesium stearate and macrogol 6000.

As will be understood by the person skilled in the art, the number "6000" after polyethylene glycol refers to the average molecular weight of the polyethylene glycol.

Usually, the pharmaceutical composition according to the present invention comprises 0.0 to 5.50% per weight of lubricant with respect to the total weight of the core of the tablet.

Preferably, the pharmaceutical composition according to the present invention comprises 0.0 to 3.50% per weight of lubricant with respect to the total weight of the core of the tablet.

More preferably, the pharmaceutical composition according to the present invention comprises 0.5 to 2.0% per weight of lubricant with respect to the total weight of the core of the tablet.

The pharmaceutical composition of the invention may also comprise diluents as excipient within the core of the tablet The term "diluent" as used herein is defined as an agent used as filler in order to achieve the desired tablet volume or weight. The diluent may be present in the pharmaceutical composition in the form of a single compound or in the form of a mixture of compounds. If the properties of the diluent are enough, it could also play a functional role in the formulation and one could get rid of one or several other specific processing aid excipients.

Examples of diluent are, but not limited to, lactose, starch, pregelatinized starch, microcrystalline cellulose, silicified microcrystalline cellulose, cellulose acetate, dextrose, mannitol, sodium phosphate, potassium phosphate, calcium phosphate, fructose, maltose, sorbitol, or sucrose.

Preferred diluant are microcrystalline cellulose, lactose and starch.

Usually, the pharmaceutical composition according to the present invention comprises 0.0 to 75% per weight of diluent with respect to the total weight of the core of the tablet.

Preferably, the pharmaceutical composition according to the present invention comprises 0 to 60% per weight of diluent with respect to the total weight of the core of the tablet.

More preferably, the pharmaceutical composition according to the present invention comprises 0 to 40% per weight of diluent with respect to the total weight of the core of the tablet.

The pharmaceutical composition of the invention may also comprise binders as excipient within the core of the tablet.

The term "binder" as used herein is defined as an agent used to increase the cohesion of the granules during the compression, in order to obtain tablets with a defined hardness, or to act as processing aid during a granulation process. The binder may be present in the pharmaceutical composition in the form of a single compound or in the form of a mixture of compounds.

When the binder is a water soluble polymer, usually it shows viscosity values lower than 500 mPa·s in 2 percent aqueous solution. Preferably, water soluble binders show viscosity values lower than 100 mPa·s in 2 percent aqueous solution (20° C.).

Examples of binders are, but not limited to, starch, microcrystalline cellulose, silicified microcystalline cellulose, carboxymethylcellulose, hydroxypropyl methylcellulose, sucrose, dextrin, maltodextrin, sorbitol, polyvinylpirrolidone (PVP), methylcellulose, pregelatinized starch.

Preferred binders are microcystalline cellulose for direct compression or dry granulation tablets, and pregelatinized starch, hydroxypropylmethyl cellulose and polyvinylpirrolidone for wet granulation tablets.

Usually, the pharmaceutical composition according to the present invention comprises 0.0 to 80% per weight of binder with respect to the total weight of the core of the tablet.

Preferably, the pharmaceutical composition according to the present invention comprises 1 to 70% per weight of binder with respect to the total weight of the core of the tablet.

More preferably, the pharmaceutical composition according to the present invention comprises 2 to 60% per weight of binder with respect to the total weight of the core of the tablet.

In one embodiment of the invention, the pharmaceutical composition comprises Brivaracetam as active ingredient and
  5.0 to 80.0% of hydrophilic matrix agent,
  0.0 to 75% of diluent,
  0.0 to 80% of binder,
  0.0 to 3.0% of gliding agent, and
  0.0 to 5.50% of lubricant,
with respect to the total weight of the core of the tablet.

Particularly, the present invention relates to a pharmaceutical composition comprising Brivaracetam as active ingredient and
  10.0 to 75.0% of hydrophilic matrix agent,
  0.0 to 60% of diluent,
  1.0 to 70% of binder,
  0.0 to 2.5% of gliding agent, and
  0.0 to 3.5% of lubricant,
with respect to the total weight of the core of the tablet.

Preferably, the present invention relates to a pharmaceutical composition comprising Brivaracetam as active ingredient and
  15.0 to 70% of hydrophilic matrix agent,
  0.0 to 40% of diluent,
  2.0 to 60% of binder,
  0.0 to 2.0% of gliding agent, and
  0.4 to 1.3% of lubricant,
with respect to the total weight of the core of the tablet.

In a particular embodiment for direct compression tablet, the present invention relates to a pharmaceutical composition comprising Brivaracetam as active ingredient and
- 5.0 to 80% of hydroxypropylmethylcellulose,
- 0.0 to 75% of lactose,
- 0.0 to 80% of microcrystalline cellulose,
- 0.0 to 3.0% of anhydrous colloidal silica, and
- 0.0 to 5.5% of magnesium stearate, with respect to the total weight of the core of the tablet.

Usually, in a particular embodiment for direct compression tablet, the present invention relates to a pharmaceutical composition comprising Brivaracetam as active ingredient and
- 10 to 75% of hydroxypropylmethylcellulose,
- 0.0 to 60% of lactose,
- 1.0 to 70% of microcrystalline cellulose,
- 0.0 to 2.5% of anhydrous colloidal silica, and
- 0.0 to 3.5% of magnesium stearate, with respect to the total weight of the core of the tablet.

Particularly, in a particular embodiment for direct compression tablet, the present invention relates to a pharmaceutical composition comprising Brivaracetam as active ingredient and
- 25 to 60% of hydroxypropylmethylcellulose,
- 0.0 to 40% of lactose,
- 2.0 to 60% of microcrystalline cellulose,
- 0.0 to 2.0% of anhydrous colloidal silica, and
- 0.4 to 1.3% of magnesium stearate, with respect to the total weight of the core of the tablet.

In a particular embodiment for wet granulation tablets, the present invention relates to a pharmaceutical composition comprising Brivaracetam as active ingredient and
- 5.0 to 80% of hydroxypropylmethylcellulose,
- 0 to 5% of polyvinylpyrolidone,
- 0.0 to 80% of microcrystalline cellulose,
- 0.0 to 40% of lactose,
- 0.0 to 3.0% of anhydrous colloidal silica, and
- 0.0 to 5.5% of magnesium stearate, with respect to the total weight of the core of the tablet.

Usually, in a particular embodiment for wet granulation tablet, the present invention relates to a pharmaceutical composition comprising Brivaracetam as active ingredient and
- 10 to 75% of hydroxypropylmethylcellulose,
- 0 to 3% of polyvinylpyrolidone,
- 0.0 to 30% of lactose,
- 1.0 to 70% of microcrystalline cellulose,
- 0.0 to 2.5% of anhydrous colloidal silica, and
- 0.0 to 3.5% of magnesium stearate, with respect to the total weight of the core of the tablet.

Particularly, in a particular embodiment for wet granulation tablet, the present invention relates to a pharmaceutical composition comprising Brivaracetam as active ingredient and
- 25 to 60% of hydroxypropylmethylcellulose,
- 0 to 2% of polyvinylpyrolidone,
- 0.0 to 20% of lactose,
- 2.0 to 60% of microcrystalline cellulose,
- 0.0 to 2.0% of anhydrous colloidal silica, and
- 0.4 to 1.3% of magnesium stearate, with respect to the total weight of the core of the tablet.

In another particular embodiment for wet granulation tablets, the present invention relates to a pharmaceutical composition comprising Brivaracetam as active ingredient and
- 5.0 to 80% of hydroxypropylmethylcellulose,
- 0.0 to 80% of microcrystalline cellulose,
- 0.0 to 75% of lactose,
- 0.0 to 40% of pregelatinized maize starch,
- 0.0 to 3.0% of anhydrous colloidal silica, and
- 0.0 to 5.5% of magnesium stearate, with respect to the total weight of the core of the tablet.

Usually, in a particular embodiment for wet granulation tablet, the present invention relates to a pharmaceutical composition comprising Brivaracetam as active ingredient and
- 10 to 75% of hydroxypropylmethylcellulose,
- 1.0 to 70% of microcrystalline cellulose,
- 0.0 to 60% of lactose,
- 0.0 to 30% of pregelatinized maize starch,
- 0.0 to 2.5% per weight of anhydrous colloidal silica, and
- 0.0 to 3.5% per weight of magnesium stearate, with respect to the total weight of the core of the tablet.

Particularly, in a particular embodiment for wet granulation tablet, the present invention relates to a pharmaceutical composition comprising Brivaracetam as active ingredient and
- 25 to 60% of hydroxypropylmethylcellulose,
- 2.0 to 60% of microcrystalline cellulose,
- 0.0 to 40% of lactose,
- 0.0 to 20% of pregelatinized maize starch,
- 0.0 to 2.0% of anhydrous colloidal silica, and
- 0.4 to 1.3% of magnesium stearate, with respect to the total weight of the core of the tablet.

The pharmaceutical composition of the invention can be manufactured by any process according to conventional methods known by the man skilled in the art. Examples of processes are direct compression, dry granulation, wet granulation, melt granulation.

For wet granulation processes, the active ingredient could either be placed within the internal phase as a solid material, in the external phase as a solid material, be dissolved in the liquid phase or a mix of thereof. The hydrophilic agents could either be incorporated in the liquid phase, in the internal phase, as solid materials, or in the external phase, or a mix of thereof.

In a specific embodiment of the invention, tablets are produced by compressing a mix of granules (the internal phase) and other excipients (the external phase). The granules are prepared through a wet granulation process, by dissolving Brivaracetam into a water solution and by spraying it into a powder bed.

Usually, in a specific embodiment, the weight ratio between the powder bed and water ranges from 1.0 to 10.0, the weight ratio between the powder bed and Brivaracetam ranges from 1.0 to 20.0 and the Brivaracetam concentration in the solution ranges from 5% to 45% (in weight %).

Particularly, in a specific embodiment, the weight ratio between the powder bed and water ranges from 1.0 to 5.0, the weight ratio between the powder bed and Brivaracetam ranges from 2.0 to 10.0 and the Brivaracetam concentration in the solution ranges from 15% to 40% (in weight %).

More particularly, in a specific embodiment, the weight ratio between the powder bed and water ranges from 1.2 to 2.5, the weight ratio between the powder bed and Brivaracetam ranges from 2.5 to 5.0 and the Brivaracetam concentration in the solution ranges from 20% to 35% (in weight %).

In a specific embodiment of the invention, wet granulation process was found to bring an unexpected positive effect on the drug dissolution, when compared to direct compression process. This unexpected phenomenon could be explained by a synergetic effect of microcrystalline cellulose and hydroxypropylmethylcellulose, as Brivaracetam is finely dispersed and/or entrapped in the internal phase. Consequently, smaller pores are created by the dissolution of the active pharmaceutical ingredient, and it has also to diffuse out of the microcrystalline granules. Hence, the dissolution of Brivaracetam is further slowed down.

So, the invention relates to a solid pharmaceutical composition comprising granules and an external phase, said granules containing brivaracetam, as active ingredient, and said external phase containing 5% to 80% per weight of at least one hydrophilic matrix agent, with respect to the total weight of the core of the tablet.

Usually, the granule comprises at least a diluent, excipient as defined above. Usually, the external phase comprises at least a lubricant, excipient as defined above. Usually, the external phase may also comprise at least a gliding agent, excipient as defined above. Usually, the external phase may comprise at least a diluent, excipient as defined above.

The process may comprise a further coating step in which a solvent, preferably purified water, is added to the coating agent and resulting suspension is sprayed on the core of the tablet.

In another aspect the present invention relates to a pharmaceutical composition comprising Brivaracetam useful for the treatment or prevention of a disease.

By the term "disease", we understand a disease selected from the group consisting of epileptogenesis, seizure disorders, convulsions, Parkinson's disease, dyskinesia induced by dopamine replacement therapy, tardive dyskinesia induced by administration of neuroleptic drugs, Huntington Chorea, and other neurological disorders including bipolar disorders, mania, depression, anxiety, attention deficit hyperactivity disorder (ADHD), migraine, cluster headache, trigeminal and other neuralgia, chronic pain, neuropathic pain, cerebral ischemia, cardiac arrhythmia, myotonia, cocaine and other substance abuse (e.g. alcohol, benzodiazepines, opiates, marijuana, barbiturates, amphetamines, other stimulants), stroke, myoclonus, dystonia, dyskinesia, tremor, essential tremor, simple or complex tics, Tourette syndrome, restless leg syndrome and other movement disorders, neonatal cerebral haemorrhage, amyotrophic lateral sclerosis, spasticity and degenerative diseases, bronchial asthma, asthmatic status and allergic bronchitis, asthmatic syndrome, bronchial hyperreactivity and bronchospastic syndromes as well as allergic and vasomotor rhinitis and rhinoconjunctivitis.

The term "treatment" as used herein, includes curative treatment and prophylactic treatment.

By "curative" is meant efficacy in treating a current symptomatic episode of a disorder or condition.

By "prophylactic" is meant prevention of the occurrence or recurrence of a disorder or condition.

The present invention concerns also a method for treatment of a human patient by using the pharmaceutical composition.

The present invention concerns also the pharmaceutical composition for use as a medicament for curing the said disease.

The present invention concerns also the use of the pharmaceutical composition for the manufacture of a medicament for a therapeutic application in the said disease.

Preferably said disease is selected from the group consisting essentially of epilepsy, Parkinson's disease, dyskinesia, migraine, tremor, essential tremor, bipolar disorders, chronic pain, neuropathic pain, or bronchial, asthmatic or allergic conditions. More preferably said disease is epilepsy.

The present invention concerns also a method for manufacturing a medicament intended for therapeutic application in the said disease, characterized in that the pharmaceutical composition according to the present invention is used.

The present invention is also directed to methods of treating humans to alleviate disease by the administration of the pharmaceutical composition.

The following examples are provided for illustrative purposes only and are not intended, nor should they be construed, as limiting the invention in any manner. Those skilled in the art will appreciate that routine variations and modifications of the following examples can be made without exceeding the spirit or scope of the invention.

EXAMPLES

Example 1

300 mg round convex tablets A, B, and C are prepared by direct compression process according to the invention with the following core compositions (Table 1).

TABLE 1

Core compositions of tablets A, B and C.

| Ingredients | Tablet A | | Tablet B | | Tablet C | |
| --- | --- | --- | --- | --- | --- | --- |
| | mg | % | mg | % | mg | % |
| Brivaracetam | 50 | 16.7 | 50 | 16.7 | 50 | 16.7 |
| Methocel ® K15 MCR | 90 | 30 | 135 | 45 | 225 | 75 |
| Tablettose ® 80 | 103.7 | 34.6 | 73.7 | 24.6 | 13.7 | 4.6 |
| Avicel ® PH102 | 51.8 | 17.3 | 36.8 | 12.3 | 6.8 | 2.3 |
| Aerosil ® 200 | 1.5 | 0.5 | 1.5 | 0.5 | 1.5 | 0.5 |
| Magnesium stearate | 3 | 1 | 3 | 1 | 3 | 1 |
| Tablet diameter (mm) | 9 | | 9 | | 9 | |
| Specific Surface area ($mm^{-1}$) | 0.9 | | 0.9 | | 0.9 | |

Hydropropyl methylcellulose sold under the trademark Methocel® is used as a hydrophilic matrix agent. The compound Methocel® K15 M CRP (trade name) is also known as hypromellose which is a hydrophilic polymer. The viscosity of an aqueous solution in water for 2% (w/w) of the compound Methocel® K 15M CRP is about 15000 mPa·s, the grade K (methoxy and hydroxypropy content) is preferred for a better hydration rate of the polymer.

Lactose is sold under the trademark Tablettose® 80; it is used as filler.

Microcrystalline cellulose is sold under the trademark Avicel® PH102. It is used as tablet binder.

Anhydrous colloidal silica is sold under the trademark Aerosil® 200. it is used as gliding agent.

Magnesium stearate is used as a lubricant.

Tablets A, B and C show a sustained release of the Brivaracetam what comply with the in vitro dissolution requirements.

TABLE 2 results in %

| | Time Hours | | |
| --- | --- | --- | --- |
| | 1.00.00 | 4.00.00 | 16.00.00 |
| Tablet A | 30 | 66 | 96 |
| Tablet B | 25 | 57 | 96 |
| Tablet C | 14 | 40 | 86 |

The in vitro dissolution profiles in water of tablets A, B and C were determined according to the USP <711> (apparatus no 2, 50 rpm, aqueous medium 900 mL) over an interval of time of 16 h. The dissolution was conducted at 37° C. in a pH 6.4 phosphate buffer.

Example 2

300 mg round convex tablets D are prepared by direct compression process according to the invention with the following core compositions (Table 3).

TABLE 3

Core compositions of tablets D

| Ingredients | Tablet D mg | Tablet D % |
|---|---|---|
| Brivaracetam | 50 | 16.7 |
| Polyox ® WSR 303 | 135 | 45 |
| Tablettose ® 80 | 73.7 | 24.6 |
| Avicel ® PH102 | 38.6 | 12.3 |
| Aerosil ® 200 | 1.5 | 0.5 |
| Magnesium stearate | 3 | 1 |
| Tablet diameter (mm) | 9 | |
| Specific Surface area (mm$^{-1}$) | 0.9 | |

Polyox® WSR 303 is a brand name for a high molecular weight polyethylene oxide that is used as a hydrophilic matrix agent. The viscosity of an aqueous solution in water for 1% (w/w) of the compound Polyox® WSR 303 is about 10000 mPa·s.

Lactose is sold under the trademark Tablettose® 80; it is used as filler.

Microcrystalline cellulose is sold under the trademark Avicel® PH102. It is used as tablet binder.

Anhydrous colloidal silica is sold under the trademark Aerosil® 200. it is used as gliding agent.

Magnesium stearate is used as a lubricant.

Tablets D show a sustained release of the Brivaracetam, what comply with the in vitro dissolution requirements.

TABLE 4 results in %

| | Time Hours | | |
|---|---|---|---|
| | 1.00.00 | 4.00.00 | 16.00.00 |
| Tablet D | 25 | 58 | 97 |

The in vitro dissolution profiles in water of tablets D are determined according to the USP <711> (apparatus no 2, 50 rpm, aqueous medium 900 mL) over an interval of time of 16 h. The dissolution was conducted at 37° C. in a pH 6.4 phosphate buffer.

Example 3

500 mg round Tablets E and F are prepared by a wet granulation process according to the invention with the following core compositions (Table 5).

TABLE 5

| | Ingredient | Role | Tablet E | Tablet F |
|---|---|---|---|---|
| Internal phase | Lycatab ® C | Binder | 0 | 42.8 mg |
| | Povidone ® K30 | Binder | 8.0 mg | 0 |
| | Lactose 100 mesh | Filler | 0 | 80.8 mg |
| | Avicel ® PH 112 | Binder | 209.5 mg | 40.4 mg |
| Granulation solution | Brivaracetam | Active ingredient | 50 mg | 20 mg |
| | Water | Wet granulation liquid | 93 ml | 45 ml |
| External phase | Methocel ® K15M CRP | Hydrophilic polymer | 225 mg | 154.8 mg |
| | Magnesium stearate | Lubricant | 5 mg | 3.4 mg |
| | Aerosil ® 200 | Gliding agent | 2.5 mg | 1.7 mg |
| | Surface area | | 0.7 mm$^{-1}$ | 0.9 mm$^{-1}$ |
| | Tablet weight | | 500 mg | 349.9 mg |

The manufacturing took place in 3 main steps:

1. Brivaracetam is dissolved in purified water and sprayed up to the appropriate dose onto a powder bed.
2. The obtained granules are subsequently dried, milled and mixed with the external phase
3. The granules are compressed into tablets.

Hydropropyl methylcellulose sold under the trademark Methocel® is used as a hydrophilic matrix agent. The compound Methocel® K15 M CRP (trade name) is also known as hypromellose which is a hydrophilic polymer. The viscosity of an aqueous solution in water for 2% (w/w) of the compound Methocel® K 15M CRP is about 15000 mPa·s, the grade K (methoxy and hydroxypropy content) is preferred for a better hydration rate of the polymer.

Microcrystalline cellulose is sold under the trademark Avicel® PH112. It is used as tablet binder.

Lactose 100 mesh is used as a filler

Anhydrous colloidal silica is sold under the trademark Aerosil 200. it is used as gliding agent.

Povidone® K30 (polyvinylpyrrolidone, PVP) and Lycatab® C (pregelatinized maize starch) are binding agent Tablets E and F show a sustained release of the Brivaracetam, what comply with the in vitro dissolution requirements.

TABLE 6 results in %

| | Time (Hours) | | |
|---|---|---|---|
| | 1.00.00 | 4.00.00 | 16.00.00 |
| Tablet E | 21 | 47 | 90 |
| Tablet F | 22 | 51 | 88 |

The in vitro dissolution profiles in water of tablets E and F are determined according to the USP <711> (apparatus no 2, 50 rpm, aqueous medium 900 mL) over an interval of time of 16 h. The dissolution was conducted at 37° C. in a pH 6.4 phosphate buffer.

Example 4

352 mg round Tablets G are prepared by a wet granulation process according to the invention with the following core compositions (Table 7).

TABLE 7 tablet G

| Step | Ingredient | Role | Quantity/tablet |
|---|---|---|---|
| Internal phase Granulation Solution | Avicel ® PH 102 Brivaracetam H₂O | Binder Active ingredient wet granulation liquid | 169.2 mg 50.0 mg 116.2 mg |
| Total Final granule | | | 219.2 mg |
| Internal phase External phase | Granules Methocel ® K15M Aerosil ® 200 Tablettose ® 80 Mg Stearate | Hydrophilic polymer Gliding agent Filler Lubricant | 219.2 mg 96.00 mg 1.6 mg 32 mg 3.2 mg |
| Total | | | 352.0 mg |

The manufacturing took place in 3 main steps:

1. Brivaracetam is dissolved in purified water and sprayed up to the appropriate dose onto a powder bed.

2. The obtained granules are subsequently dried, milled and mixed with the external phase.

3. The granules are compressed into tablets.

Hydropropyl methylcellulose sold under the trademark Methocel® is used as a hydrophilic matrix agent. The compound Methocel® K15 M CRP (trade name) is also known as hypromellose which is a hydrophilic polymer. The viscosity of an aqueous solution in water for 2% (w/w) of the compound Methocel® K 15M CRP is about 15000 mPa·s, the grade K (methoxy and hydroxypropy content) is preferred for a better hydration rate of the polymer.

Microcrystalline cellulose is sold under the trademark Avicel® PH102. It is used as tablet binder.

Tablettose® 80 is a monohydrate lactose used as a filler.

Anhydrous colloidal silica is sold under the trademark Aerosil® 200. it is used as gliding agent.

Tablets G show a sustained release of the Brivaracetam, what comply with the in vitro dissolution requirements.

TABLE 8 results in %

| | Time (Hours) | | |
|---|---|---|---|
| | 1.00.00 | 4.00.00 | 16.00.00 |
| Tablet G | 25 | 56 | 96 |

The in vitro dissolution profiles in water of tablets G are determined according to the USP <711> (apparatus no 2, 50 rpm, aqueous medium 900 mL) over an interval of time of 16 h. The dissolution was conducted at 37° C. in a pH 6.4 phosphate buffer.

Example 5

360 mg round Tablets H are prepared by a wet granulation process according to the invention with the following core compositions (Table 9).

TABLE 9

| Step | Ingredient | Role | Quantity/tablet |
|---|---|---|---|
| Internal phase Spray Solution | Avicel ® PH 102 Brivaracetam H₂O | Binder Active ingredient wet granulation liquid | 169.2 mg 50.0 mg 116.2 mg |
| total Final granule | | | 219.2 mg |
| Internal phase External phase | Granules Methocel ® K15M Aerosil ® 200 Lactose spray dried Mg Stearate | Hydrophilic polymer Gliding agent Filler Lubricant | 219.2 mg 106 mg 1.8 mg 30 mg 3.0 mg |
| Total | | | 360.00 mg |

The manufacturing took place in 3 main steps:

1. Brivaracetam is dissolved in purified water and sprayed up to the appropriate dose onto a powder bed.

2. The obtained granules are subsequently dried, milled and mixed with the external phase 3. The granules are compressed into tablets.

Hydropropyl methylcellulose sold under the trademark Methocel® is used as a hydrophilic matrix agent. The compound Methocel® K15 M CRP (trade name) is also known as hypromellose which is a hydrophilic polymer. The viscosity of an aqueous solution in water for 2% (w/w) of the compound Methocel® K 15M CRP is about 15000 mPa·s, the grade K (methoxy and hydroxypropy content) is preferred for a better hydration rate of the polymer.

Microcrystalline cellulose is sold under the trademark Avicel® PH102. It is used as tablet binder.

Spray dried lactose is used as a filler.

Anhydrous colloidal silica is sold under the trademark Aerosil® 200. it is used as gliding agent.

Tablets H show a sustained release of the Brivaracetam, what comply with the in vitro dissolution requirements.

TABLE 10 results in %

| | Time (Hours) | | |
|---|---|---|---|
| | 1.00.00 | 4.00.00 | 16.00.00 |
| Tablet H | 24 | 55 | 96 |

The in vitro dissolution profiles in water of tablets H are determined according to the USP <711> (apparatus no 2, 50 rpm, aqueous medium 900 mL) over an interval of time of 16 h. The dissolution is conducted at 37° C. in a pH 6.4 phosphate buffer.

The wet granulation process and formulation used for Tablets G & H gives tablets with a final weight similar to Tablets B. Surprisingly, the required level of hydrophilic polymer, required to achieve a given dissolution profile, is about 50% lower for formulation G and H, than that required for formulation B.

The wet granulation process is found to bring an unexpected positive effect on the drug dissolution, when compared to direct compression process. As shown in examples 4 and 5, tablet G and H, the level of hydrophilic polymer could be decreased by ca. 50% when compared to Example 1, Tablet B, while keeping an equivalent in vitro dissolution profile. This unexpected phenomenon could be explained by a synergistic effect of microcrystalline cellulose and hydroxypropylmethylcellulose, as Brivaracetam is finely dispersed and/or entrapped in the internal phase. Consequently, smaller pores are created by the dissolution of the active pharmaceutical ingredient, and it has also to diffuse out of the microcrystalline granules. Hence, the dissolution of Brivaracetam is further slowed down.

Example 6

720 mg round Tablets I are prepared by a wet granulation process according to the invention with the following core compositions (Table 11).

TABLE 11

| Step | Ingredient | Role | Quantity/tablet |
|---|---|---|---|
| Internal phase Spray Solution | Avicel ® PH 102 | Binder | 338.4 mg |
| | Brivaracetam | Active ingredient | 100.0 mg |
| | H₂O | Wet granulation liquid | 232.4 mg |
| total Final granule | | | 438.4 mg |
| Internal phase | Granules | | 438.4 mg |
| External phase | Methocel ® K15M | Hydrophilic polymer | 212 mg |
| | Aerosil ® 200 | Gliding agent | 3.6 mg |
| | Lactose spray dried | Filler | 60 mg |
| | Mg Stearate | Lubricant | 6.0 mg |
| Total | | | 720.0 mg |

The manufacturing took place in 3 main steps:
1. Brivaracetam is dissolved in purified water and sprayed up to the appropriate dose onto a powder bed.
2. The obtained granules are subsequently dried, milled and mixed with the external phase
3. The granules are compressed into tablets.

Hydropropyl methylcellulose sold under the trademark Methocel® is used as a hydrophilic matrix agent. The compound Methocel® K15 M CRP (trade name) is also known as hypromellose which is a hydrophilic polymer. The viscosity of an aqueous solution in water for 2% (w/w) of the compound Methocel® K 15M CRP is about 15000 mPa·s, the grade K (methoxy and hydroxypropy content) is preferred for a better hydration rate of the polymer.

Microcrystalline cellulose is sold under the trademark Avicel® PH102. It is used as tablet binder.

Spray dried lactose is used as a filler.

Anhydrous colloidal silica is sold under the trademark Aerosil® 200. it is used as gliding agent.

Tablets I show a sustained release of the Brivaracetam, what comply with the in vitro dissolution requirements.

TABLE 12

| results in % | | | |
|---|---|---|---|
| | Time (Hours) | | |
| | 1.00.00 | 4.00.00 | 16.00.00 |
| Tablet I | 22 | 47 | 89 |

The in vitro dissolution profiles in water of tablets I are determined according to the USP <711> (apparatus no 2, 50 rpm, aqueous medium 900 mL) over an interval of time of 16 h. The dissolution is conducted at 37° C. in a pH 6.4 phosphate buffer.

The invention claimed is:

1. A sustained release pharmaceutical composition in the form of a tablet comprising Brivaracetam and, within the core of the tablet, 5% to 80% per weight of at least one hydrophilic matrix agent with respect to the total weight of the core of the tablet, wherein the hydrophilic matrix agent is hydroxypropyl methylcellulose having a viscosity of more than 100 mPa·s in 2 percent aqueous solution (20° C.), and wherein the specific surface area of the core tablet is between 2 $mm^{-1}$ and 0.3 $mm^{-1}$.

2. The pharmaceutical composition according to claim 1 comprising granules and an external phase, said granules containing brivaracetam and said external phase containing at least one hydrophilic matrix agent.

3. The pharmaceutical composition according to claim 1, comprising brivaracetam and a water dispersible, rate controlling polymer as hydrophilic matrix agent.

4. The pharmaceutical composition according to claim 1, comprising 20 to 60% per weight of hydrophilic matrix agent.

5. The pharmaceutical composition according to claim 1, comprising 0.0 to 1.5% per weight of gliding agent with respect to the total weight of the core of the tablet.

6. The pharmaceutical composition according to claim 1, comprising 0.5 to 2.0% per weight of lubricant with respect to the total weight of the core of the tablet.

7. The pharmaceutical composition according to claim 1, comprising 1 to 70% per weight of binder with respect to the total weight of the core of the tablet.

8. The pharmaceutical composition according to claim 7, comprising, as binder, a water soluble polymer having viscosity values lower than 500 mPa·s in 2 percent aqueous solution.

9. The pharmaceutical composition according to claim 1, comprising
   0.0 to 75% of diluent,
   0.0 to 80% of binder,
   0.0 to 3.0% of gliding agent, and
   0.0 to 5.5% of lubricant,
with respect to the total weight of the core of the tablet.

10. The pharmaceutical composition according to claim 1, comprising
    0.0 to 75% of lactose,
    0.0 to 80% of microcrystalline cellulose,
    0.0 to 3.0% of anhydrous colloidal silica, and
    0.0 to 5.5% of magnesium stearate,
with respect to the total weight of the core of the tablet;
wherein the composition is prepared by direct compression.

11. The pharmaceutical composition according to claim 1, comprising
    0.0 to 80% of microcrystalline cellulose,
    0.0 to 40% of lactose,
    0.0 to 5% of polyvinylpyrolidone,
    0.0 to 3.0% of anhydrous colloidal silica, and
    0.0 to 5.5% of magnesium stearate,
with respect to the total weight of the core of the tablet;
wherein the composition is prepared by wet granulation.

12. The pharmaceutical composition according to claim 1, comprising
    0.0 to 80% of microcrystalline cellulose,
    0.0 to 75% of lactose,
    0.0 to 40% of pregelatinized maize starch,
    0.0 to 3.0% of anhydrous colloidal silica, and
    0.0 to 5.5% of magnesium stearate,
with respect to the total weight of the core of the tablet;
wherein the composition is prepared by wet granulation.

* * * * *

UNITED STATES PATENT AND TRADEMARK OFFICE
CERTIFICATE OF CORRECTION

| | |
|---|---|
| PATENT NO. | : 8,435,564 B2 |
| APPLICATION NO. | : 12/993704 |
| DATED | : May 7, 2013 |
| INVENTOR(S) | : Eeckman et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 197 days.

Signed and Sealed this
Fourth Day of November, 2014

Michelle K. Lee
*Deputy Director of the United States Patent and Trademark Office*